(12) United States Patent
Lee et al.

(10) Patent No.: US 8,459,098 B2
(45) Date of Patent: Jun. 11, 2013

(54) UNIVERSAL PHYSIOLOGIC SAMPLING PUMP (PSP) CAPABLE OF RAPID RESPONSE TO BREATHING

(75) Inventors: Larry Alan Lee, Westover, WV (US); Michael Martin Flemmer, Bruceton Mills, WV (US)

(73) Assignee: The United States of America, as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 643 days.

(21) Appl. No.: 12/690,550

(22) Filed: Jan. 20, 2010

(65) Prior Publication Data
US 2010/0206096 A1    Aug. 19, 2010

Related U.S. Application Data

(60) Provisional application No. 61/145,777, filed on Jan. 20, 2009.

(51) Int. Cl.
*G01N 1/24*    (2006.01)
(52) U.S. Cl.
USPC ....... 73/31.07; 73/23.3; 73/28.04; 73/863.03; 73/863.22
(58) Field of Classification Search
USPC ........... 73/863.03, 28.04, 28.3, 31.07, 863.22
See application file for complete search history.

(56) References Cited

U.S. PATENT DOCUMENTS

| | | |
|---|---|---|
| 4,375,667 A | 3/1983 | Buchan |
| 4,589,292 A | 5/1986 | Delhaye et al. |

(Continued)

FOREIGN PATENT DOCUMENTS

CA    2175843 A1    11/1996

OTHER PUBLICATIONS

Kucharski, R. *A personal dust sampler simulating variable human lung function.* British Journal of Industrial Medicine, 37: 194-196, 1980.

(Continued)

*Primary Examiner* — Hezron E Williams
*Assistant Examiner* — Paul West
(74) *Attorney, Agent, or Firm* — Grass, Krass, Sprinkle, Anderson & Citkowski, P.C.

(57) ABSTRACT

The present invention discloses a physiologic sampling pump (PSP) which uses at least one valve placed near the sampling medium to modulate air sampling to follow a person's inhalation rate and to obviate the sluggishness inherent in prior art PSPs caused by varying pump speed and by the propagation time through an air tube that connects the collection medium to prior art pumps thereby also obviating limitations inherent in system response, functionality, and accuracy. Moreover, by maintaining an essentially constant air flow through a cyclone at all times and through the collection medium while sampling, the present invention operates at known collection efficiencies, and is therefore capable of size-selective sampling of particulates as opposed to prior art PSPs that by varying the magnitude of air flow, make the separation efficiencies of pre-collection devices indeterminate and the samples worthless. When used instead with an impact sampling head, the present invention may collect total particulate as well, and may collect gases and vapors with a charcoal tube sampling head. Structural features associated with the physiological sampling pump for providing rapid response to breathing include an outer housing including a thereto-resistant case, multiple and interchangeable PSP sampling heads further including collection media and a valve(s) mounted on a valve manifold with associated tubing.

13 Claims, 6 Drawing Sheets

U.S. PATENT DOCUMENTS

| | | | |
|---|---|---|---|
| 4,941,899 A * | 7/1990 | Liu | 73/863.23 |
| 5,892,160 A | 4/1999 | Hall | |
| 6,401,520 B1 | 6/2002 | Volkwein et al. | |
| 6,435,004 B1 * | 8/2002 | Miller | 73/23.3 |
| 6,863,508 B2 * | 3/2005 | Hauser | 417/373 |
| 7,243,560 B2 | 7/2007 | Coyle et al. | |
| 2003/0031572 A1 | 2/2003 | Tearle | |

OTHER PUBLICATIONS

Satoh, T., Higashi, T., Sakurai, H., and Omae, K. *Development of a new exposure monitoring system considering pulmonary ventilation (DEM 1).* Keio Journal of Medicine, 38(4): 432-443, 1989.

Levine, M.S. *A respiration-modulated personal air sampling pump.* Applied Occupational Environmental Hygiene, 9(12): 994-1005, 1994.

Hart, C.K. *Theory and Evaluation of a new Physiologic Sampling Pump.* Disseration, Doctor of Philosophy, 1998, Department of Environmental Health, University of Washington, Seattle, WA 98195.

Paper from Journal of Environmental Monitoring entitled "Exposure assessment by phsiologic sampling pump-prediction of minute ventilation using a portable respiratory inductive plethysmograph system" by Ming-I Lin et al., Sep. 2008.

Sensidyne, LP, Gilian GilAir-5 Constant Flow Air Sampling Pump Datasheet from www.sensidyne.com accessed Apr. 7, 2008.

SKC Inc., AirChek 2000 Sample Pump information sheet, www.skcinc.com accessed Apr. 7, 2008.

Monitoring Systems GmbH, The Genius 5 information sheet, www.dioxinmonitoring.com accessed Apr. 7, 2008.

* cited by examiner

FIG. 2
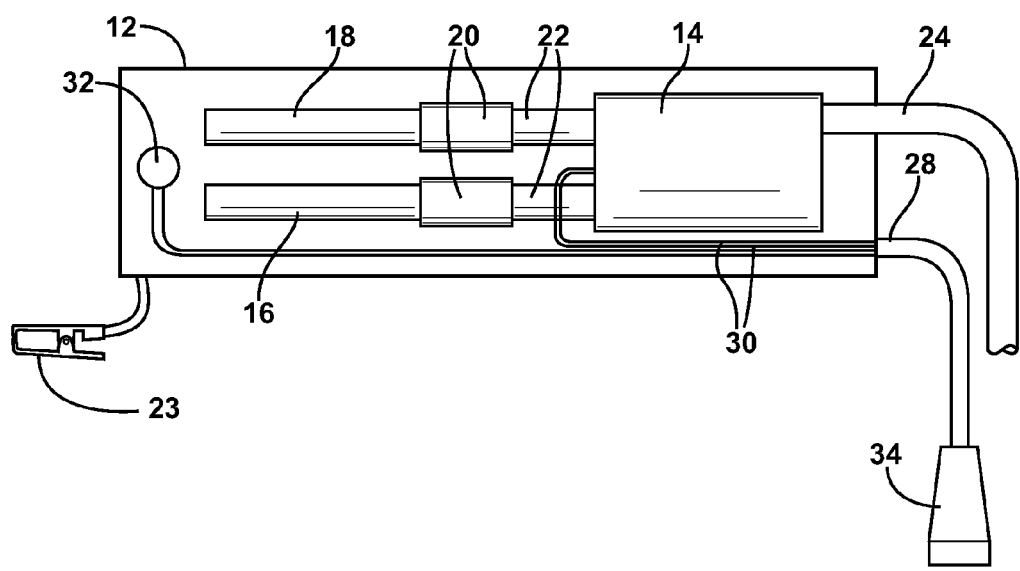
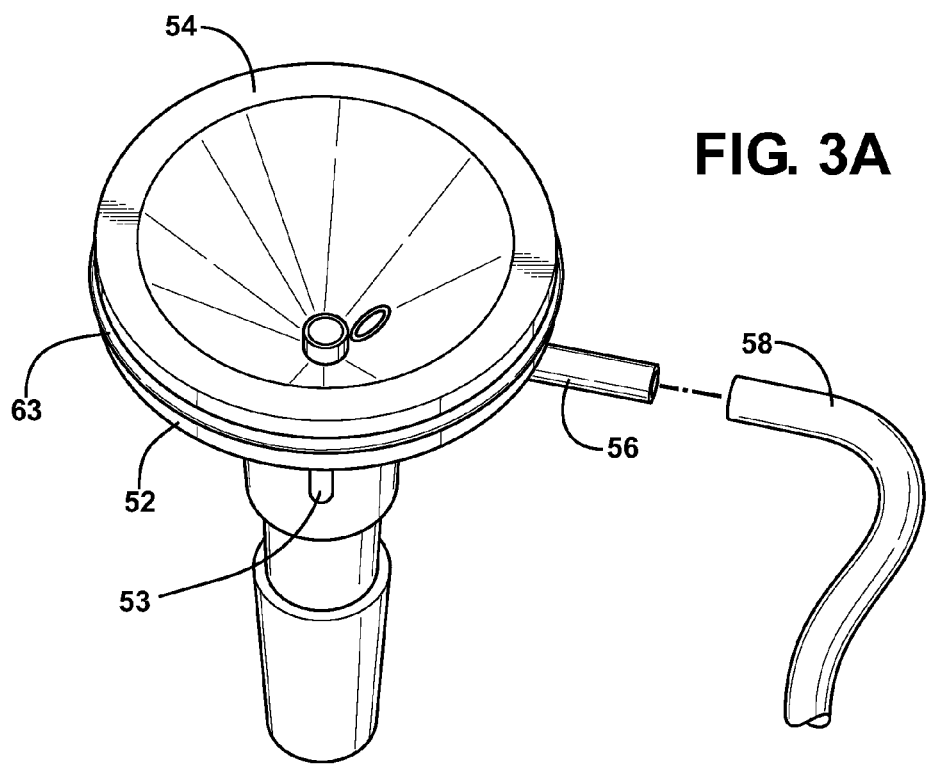
FIG. 3A

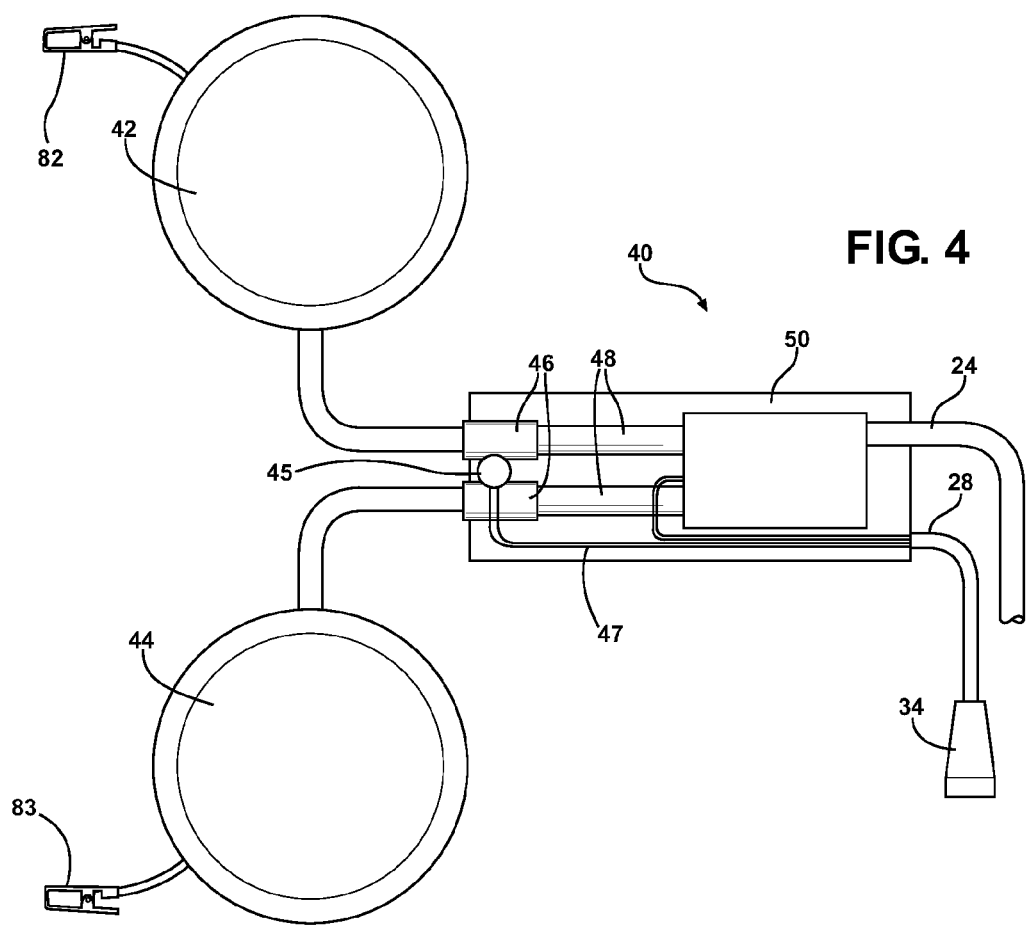

UNIVERSAL PHYSIOLOGIC SAMPLING PUMP (PSP) CAPABLE OF RAPID RESPONSE TO BREATHING

CROSS REFERENCE TO RELATED APPLICATIONS

The present application claims the benefit of U.S. Provisional Patent Application Ser. No. 61/145,777, filed Jan. 20, 2009.

STATEMENT REGARDING FEDERALLY SPONSORED RESEARCH OR DEVELOPMENT

The invention described herein may be manufactured, used, and licensed by or for the United States Government.

FIELD OF THE INVENTION

The present invention relates generally to exposure assessment and to a physiologic sampling pump (PSP) for sampling the air in proportion to an individual's inhalation, and as an improvement over prior art constant flow personal air sampling pumps, also termed traditional sampling pumps (TSP's), which cannot follow individual inhalation, but rather allows an industrial hygienist to calculate a time-weighted average (TWA) concentration of gases, vapors, or aerosol particles in the ambient air. The pump is physiologically based and samples in proportion to an individual's inhalation, with the present design further providing rapid response to breathing by maintaining a constant air flow through the pump motor, with the further addition of varying the volume of air flowing through the collection medium in proportion to an individual's inhalation by controlling the duty cycle of an in-line valve, with the further addition of using fast response valve(s) such that the air flow through the collection medium may reach the steady state about 100 times faster than prior art PSPs that attempt to proportionally change air flow by varying pump speed, and further results in collecting air samples more representative of an actual dose.

DESCRIPTION OF THE BACKGROUND ART

Previous physiologic air sampling pumps are known in the prior art. A shortcoming associated with such known sampling pumps arises from these pumps varying the pump motor speed to in turn vary the magnitude of air flowing through the sampling medium in an attempt to sample the air in proportion to the inhalation rate of a person being monitored.

As such, existing pumps cannot follow inhalation rapidly due to the transition time inherent in changing pump speed. This sluggish response is exacerbated at the collection medium because of the long (normally 3 foot long) air tube that the change in air flow must propagate through between the collection medium and the pump motor. If either a person's inhalation rate, or contaminant concentration changes quickly, the mass of contaminant collected, and therefore the derived concentration, will not represent an actual inhaled dose.

Moreover, previous physiologic sampling pumps are known which cannot be used to sample the respirable fraction of particulates. Larger non-respirable particles are deposited upon the pump filter and bias the mass being collected unless separated from the air flow upstream, such as which is accomplished by a pre-collector component such as a cyclone. As is further known, pre-collectors exhibit collection efficiencies which are a function of the effective aerodynamic diameters of the particles in the air stream, the inlet air velocity, and associated physical design of the collector body.

Furthermore, a known and constant flow is maintained in traditional sampling pumps during the entire sampling session in order to know the collection efficiency and to calculate respirable concentrations. Known PSPs also are designed that vary pump speed which in turn varies air flow to follow a subject's breathing rate, the effect of which is to vary the inlet air velocity, thereby varying the fractional collection efficiency associated with each particle size over the sampling time, and which largely renders making valid calculations of airborne concentrations of particulates impossible.

As such, and due to the variable sampling rates endemic to known physiologic pumps (such as which can also be termed as personal dust samplers), the problem of size-selective sampling remains unsolved in order to provide effective air contamination monitoring.

SUMMARY OF THE PRESENT INVENTION

The present invention discloses an improved and constant flow physiologic sampling pump (PSP) which provides for rapid valve switching in proportional response to an individual's inhalation rate, and in order to provide valid exposure assessment from representative air samples even when using a pre-collection device.

A charcoal tube sampling head is connected to the pinup and which includes at least one valve. In response to one or more physiologic signals from the individual being monitored, the PSP opens and closes the valve(s) for the first portion of each second (or other preset time period) necessary to control air flow through the charcoal tube which collects gases and/or vapors in proportion to that inhaled by the person being monitored. Following that, and for the remaining portion of each second (or other preset time period), that air flow is diverted through another "dummy" charcoal tube, such that the pump speed and the resulting air flow remains constant thereby obviating the sluggish response inherent in prior art pump motors that change pump motor speed, and further such as which compromises the functionality and accuracy of operation in previous PSPs.

Another feature of the present invention is that the charcoal tube sampling head used for gas and vapor monitoring may be disconnected from the pump and replaced with a cyclone sampling head used for size-selective collection of particulates. Connections between the sampling heads and the pump include an air tube and a cable, the wires of which carry the electronic signals used to control the valves in the sampling heads and to power and read data from a temperature sensor that may optionally be mounted in the sampling heads.

When the cyclone sampling head is connected to the pump, the present invention is configured as a constant flow physiological sampling pump (PSP) which includes at least one valve (and when more than one valve, also includes a valve manifold) such that, in response to physiologic signal(s) from the individual being monitored, the PSP opens and closes the valve(s) for the portion of each second (or other preset time period) necessary to control air flow through a sampling filter for collecting particulates in proportion to that inhaled by the person being monitored. The remainder of each second (or other preset time period) air flow is diverted through another "dummy" filter such that pump speed and the resulting air flow may remain constant and the sluggishness in response that pump motors inherently exhibit when changing speed that compromises the functionality and accuracy of operation in previous PSPs is obviated.

Other features associated with the physiological sampling pump for providing rapid response to breathing include an outer housing exhibiting a thereto-resistant case. A belt clip can be located on a back side to allow easy carrying of the pump. A quick release interface is also provided in order to exchange rechargeable batteries. Buttons are provided to select menus and various setup options displayed on the liquid crystal display (LCD), and to turn power on and off to the pump. One or more connectors are included to plug in external physiological sensors or sensing systems, or to plug in a cable to both download program revisions into the PSP as well as to upload data records to computer.

Structurally, the PSP cyclone sampling head used in particulate collection includes a modified air sampling cyclone, a valve manifold, miniature screens to protect the valve(s), and two filters mounted within individual cassettes and associated tubing.

Other features include the cyclone sampling head exhibiting a median cut-point at 4 um at a flow of 2.2 lpm (liters per minute), and which is machined so that respirable particles will exit the cyclone in the airflow via its funnel shaped outlet and be dispersed onto one of two filters, with the collection filter that is fitted over top of the cyclone funnel or onto the dummy filter that connects to a tube exiting the side of the cyclone funnel. Furthermore, the cyclone is subjected to a constant air flow by virtue of the constant air flow created by the pump being either routed by the valve(s) at all times through either the collection filter or the dummy filter, A sampling filter is placed inside a cassette dimensioned to fit onto a top of the cyclone. A tube is inserted into a hole drilled into and through one side of the cyclone funnel, just above the bottom edge of the funnel, and sealed air tight with epoxy to provide a pathway for air flow to be diverted onto the dummy filter.

When using the cyclone sampling head, an efficiency curve for collection follows from the constant air flow maintained through the cyclone, the known efficiency characteristics thereby allowing size-selective sampling of particulates in proportion to an individual's inhalation, and collection of air samples representative of individual dose and dose rate.

Other features include the outlets of the cassettes connecting to a valve manifold, the valve manifold in turn connecting to an airline, and in turn to a constant-flow pump.

An alternate implementation of a size-selective particulate sampling head, capable of similar performance as the cyclone sampling head, utilizes two impact collection devices in place of the two charcoal tubes used in the gas and vapor sampling head. The alternate implementation uses an impact sampler, such as the Institute of Occupational Medicine (TOM) impact sampler with a foam insert for pre-collection. The two impact samplers each house a filter and hang outside the sampling head enclosure and the outlet ports of the impact samplers connect via two flexible rubber tubes and replace the two charcoal tubes that are used in the gas and vapor sampling head.

BRIEF DESCRIPTION OF THE DRAWINGS

Reference will now be made to the attached drawings, when read in combination with the following detailed description, wherein like reference numerals refer to like parts throughout the several views, and in which:

FIG. 2 is an illustration of a gas and vapor sampling head according to one embodiment in use with the physiologic sampling pump and which connects to the pump by an air tube that slips onto a barbed port connector on the pump, in combination with a valve control cable exhibiting a plug on its end which fits into a mating connector on the pump;

FIG. 3A is an illustration of a PSP assembly incorporating a cyclone sampling head which may be used in substitution of the other sampling heads such as illustrated in either of FIG. 2 or 4, when size-selective collection of particulates is desired, the cyclone sampling head being connected to the pump with an air tube that slips onto a barbed port connector on the pump and a valve control cable that has a plug on the end to fit into a mating connector on the pump;

FIG. 4 is an illustration of an impact sampling head in use with the physiologic sampling pump which may be used in substitution of the other sampling heads of FIG. 2 or 3A when either size-selective or total collection of particulates is desired, and shows that the sampling head connects to the pump with an air tube that slips onto a barbed port connector on the pump and a valve control cable that has a plug on the end to fit into a mating connector on the pump;

FIG. 6a further shows air flow perturbation when the valve(s) switch air flow from the dummy filter to the PSP collection filter, and FIG. 6b shows air flow perturbation when the valve(s) switch air flow from the PSP collection filter to the dummy filter.

DETAILED DESCRIPTION OF THE PREFERRED EMBODIMENTS

Figure 1:
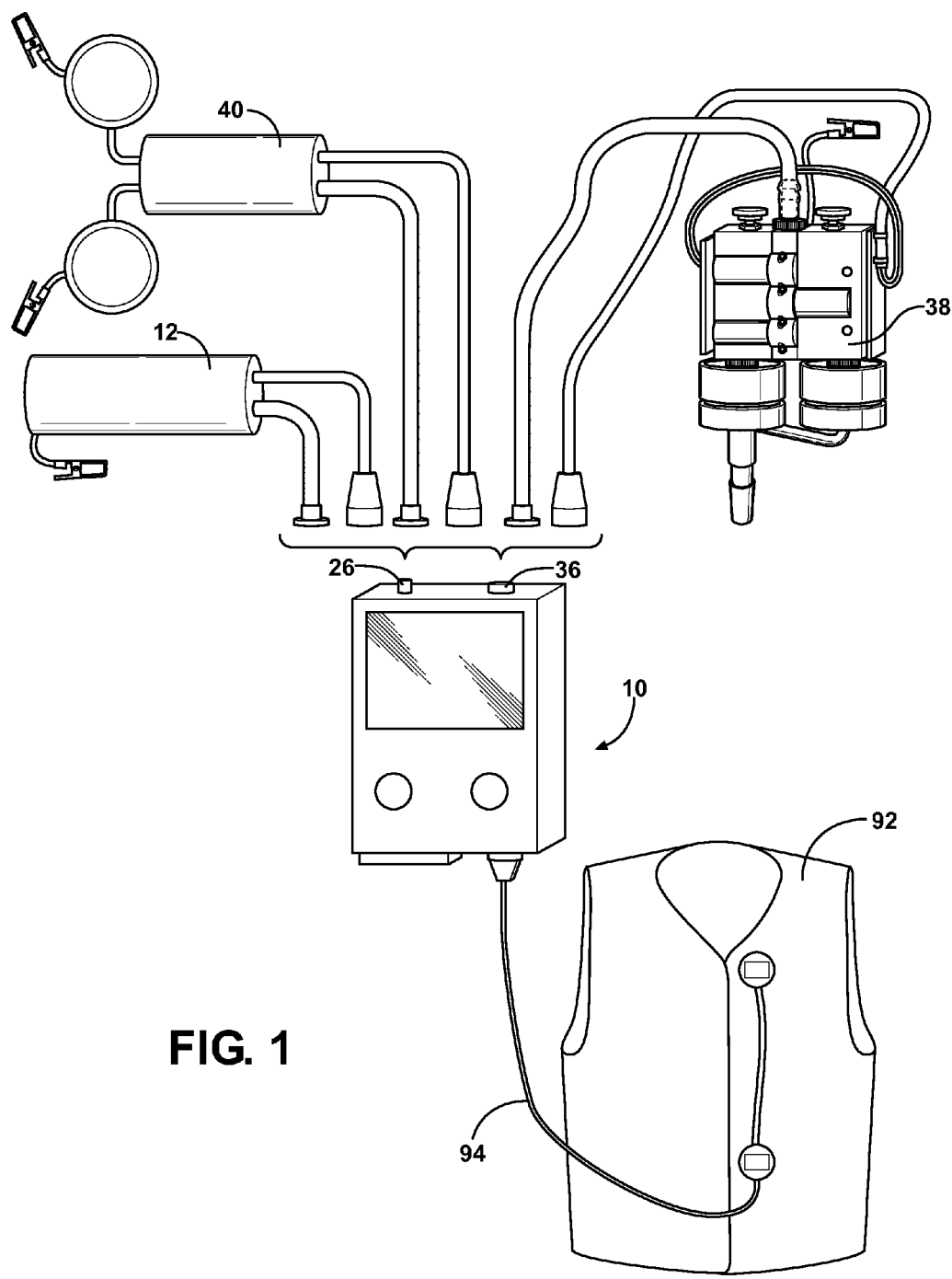
FIG. 1 is an illustration of an overall assembly view of an entire equipment inventory for sampling with the physiologic sampling pump including first, second and third alternatively configured subset sampling heads, and including electronics located inside the pump enclosure and accessible with a display, as well as illustrating a VivoMetrics, Inc. LifeShirt® system that plugs into the PSP in order to provide real time physiologic data that is processed each second by equations stored within the PSP computer program in order to estimate inhalation of the user and to control valve operation in the sampling heads, with the flexibility of the computer program embedded in the PSP, enabling other physiologic signal(s) from other hardware to be inputted into the PSP and used to estimate inhalation and to control valve operation.

As previously stated and which will be described in further detail below the present invention relates generally to exposure assessment and to physiologic sampling pumps (PSPs) for sampling the air in proportion to an individual's inhalation. More particularly, the present invention discloses a PSP having a rapid response to inhalation with multiple, interchangeable sampling heads each useful for exposure assessment of actual inhaled dose.

The sampling heads again include those that use a standard readily available charcoal tube (FIG. 2) for the collection element is useful for the collection of gases and vapors, while the other two, one of which uses a modified cyclone (FIGS. 3A and 3B) and the other which uses an impact sampler (FIG. 4) for pre-collection of particles by size, and both of which use standard readily available filter elements housed within cassettes, are useful for size-selective sampling of particulates.

Referring again to FIG. 2 a PSP charcoal tube sampling head used for collection of gases and vapors is generally illustrated at 12 includes (a) a cylindrical plastic case which opens into two halves lengthwise, but when in use is held together by a (b) machine screw, and an inlet end from which extends a clip 23 and where two charcoal tubes extend toward in order to pull in external air to be sampled, the one charcoal tube acting as the collection medium (see as shown by collection tube 16), the other (at 18) acting as a dummy collection medium to present an approximately equivalent load to the pump motor to help minimize the magnitude of any air perturbations upon valve(s) switching. Two short lengths of flexible rubber tubing are provided, both at 20 and each of which slips over the back (outlet) end of a charcoal tube 16 and 18. Opposite extending ends of the tubes 20 slip over barbed fittings which form part of a brass housing that contains two miniature 25 μm mesh screens, both at 22, used to protect the miniature valve(s) 14 from any particle breakthrough from the charcoal tubes 16 and 18. A valve port adaptor (which also may be considered a valve(s) manifold) can be provided and into which brass housings that contain the protective screens 22 screws into and from which a barbed outlet port protrudes which in turn connects an air tube 24 of suitable length (such as 3') and which connects, at the other end, to a barbed fitting 26 on the PSP enclosure. An integrated circuit temperature sensor 32 with fast response includes attached wires 30 that together with additional wires extending from the valve(s) 14 goes to the cable 28 that in turn plugs into the PSP enclosure via plug end 34 which engages a control cable connector 36 also located atop the PSP in proximity to the air tube connector fitting 26.

In operation, the air volume between the valve(s) 14 and the charcoal tubes 16 and 18 is minimized, resulting in a very short duration of air flow perturbation, i.e., resulting in a rapid response, and hence obviating the sluggish response found in prior art PSPs, that in addition to the sluggish response due to the transition time in changing pump speed, that sluggishness is exacerbated because the change in air flow must propagate the length of the air tube that connects the pump to the collection medium (typically 3 feet long and ¼ internal diameter), and causes errors and inaccuracies in collecting samples proportional to inhaled dose.

Figure 3B:
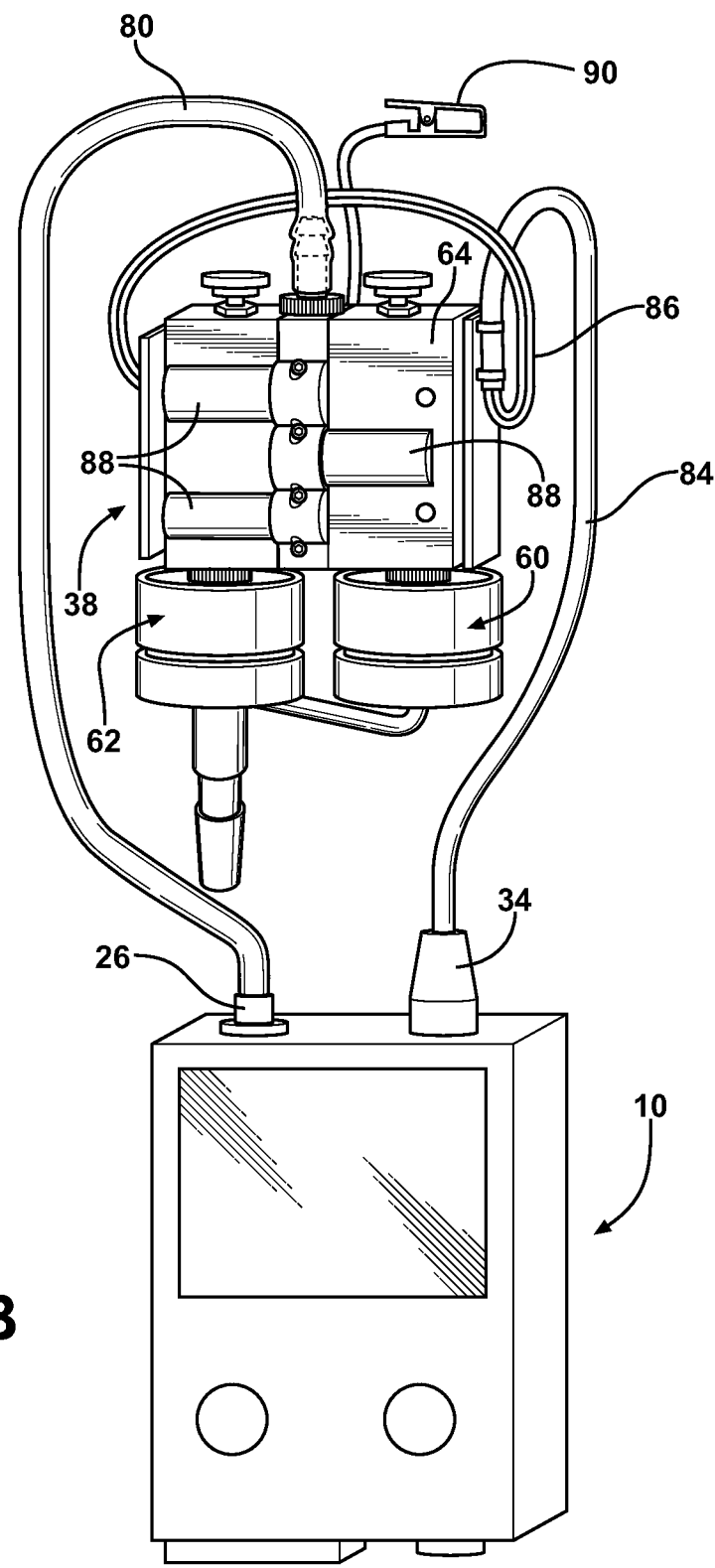
FIG. 3B is a sectional illustration of the cyclone sampling head in FIG. 3A.
Figure 5:
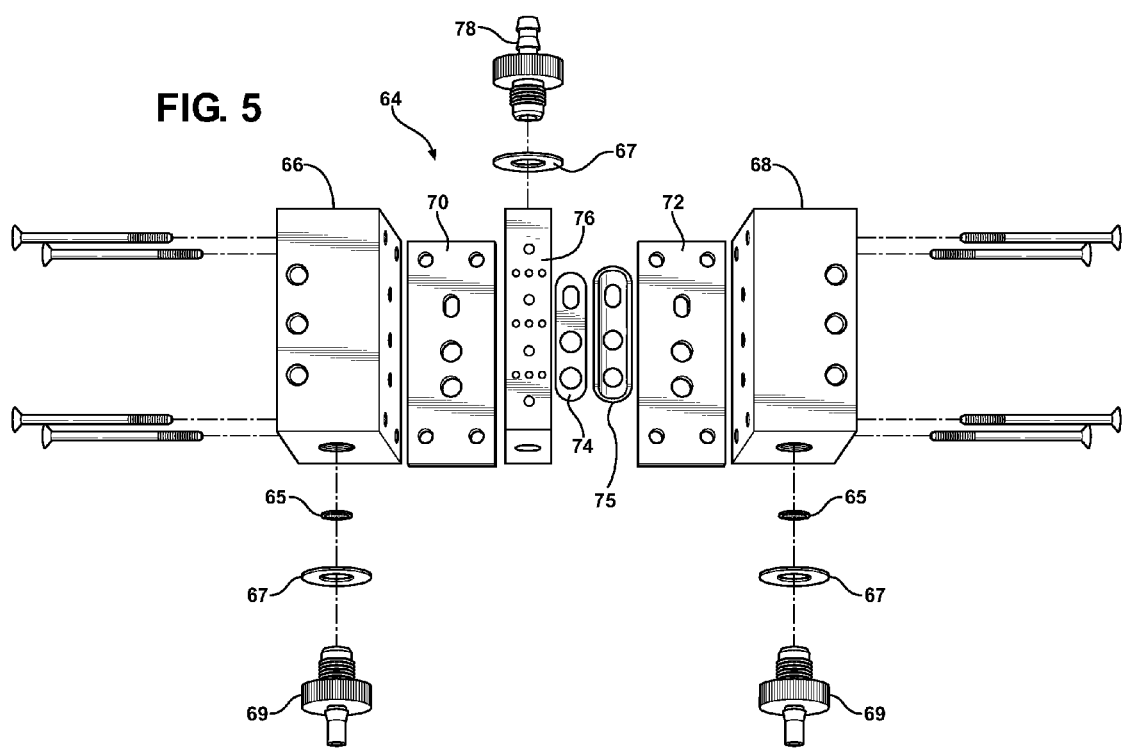
FIG. 5 is an exploded view illustration of the valve manifold shown in the assembly FIG. 3A.
Figure 6A:
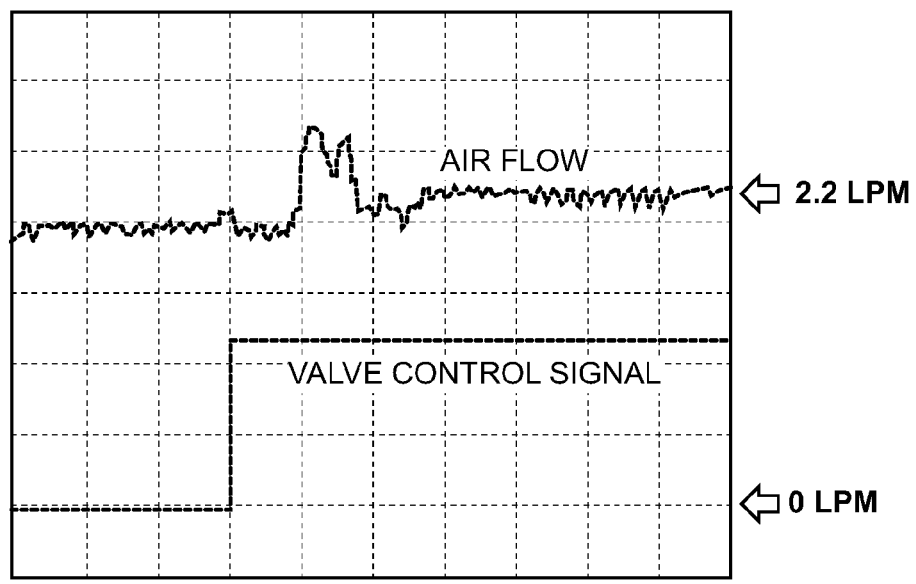
FIGS. 6A and 6B are illustrations of typical oscilloscope displays showing on upper traces air flow perturbations caused by valve switching air flow from one sampling head filter to the other, with lower traces further being representative of the valve control signals, the duration of flow perturbations being typically around 10 ms and causing insignificant changes in sampling performance.
Figure 6B:
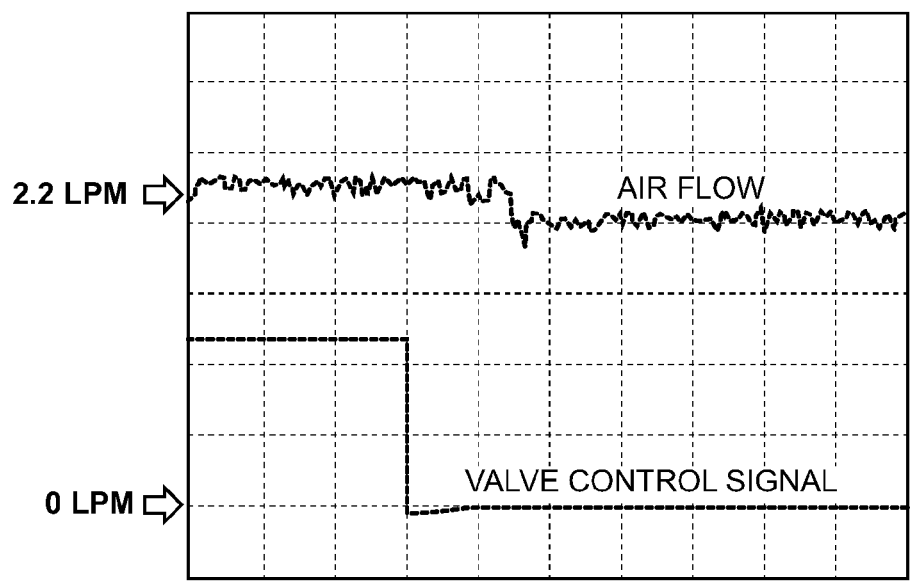

As further depicted in the oscilloscope displays of FIGS. 6A and 6B, the duration of any flow perturbance due to valve switching is of short duration (typically 10 ms out of each second). Moreover, and because the average flow over the duration of the flow perturbation tends to average to the desired constant flow by virtue of the damped nature of the flow response, and further moreover because the magnitude of the overshoot and undershoot of the flow perturbations are much less than a step transition, performance of the cyclone pre-collector, see as generally represented at 38 in FIG. 1 (and as will be described in additional detail below) in alternate representation to gas and vapor sampling head 12 and as further shown in FIGS. 3A, 3B and 5, is essentially the same as for the same cyclone when never being subjected to these perturbations, the effect of which is to preserve the known and characterized separation characteristics of the cyclone and thereby allow the cyclone to be used for size selective sampling with the PSP.

Moreover, due to the rapid response of the valve(s) (typically 3 ms) when the valve(s) switches air flow from going through the PSP charcoal tube 16 in the gas and vapor sampling head 12 (or from going through the PSP impact sampler in the alternate implementation of the size-selective particulate sampling head) to going through the dummy charcoal tube 18 in the gas and vapor sampling head (or to going through the dummy impact sampler in the alternate implementation of the size-selective particulate sampling head) air flow and inlet velocity change almost instantaneously from zero to the steady state magnitudes, thereby preserving the performance characteristics of the sampling essentially as if no switching of air flow occurred, the effect of which is that both the gas and vapor and the alternate particulate sampling heads may be used for physiologic sampling.

The NIOSH pump 10 is particularly directed to size selective sampling of aerosols, as well as gas and vapors and total particulates. No physiological sampling pumps have, to date, attempted to accomplish size selective sampling of particulates. Additionally, calibrated valves are used to obviate pump sluggishness that has limited the system response and accuracy of prior art. Technologies that provide minute ventilation ($\dot{v}_E$) of subjects in real time may therefore be used to the limit of their own accuracies to sample inhalation exposures.

Calibration of the valve(s) reduces or eliminates error in collecting samples proportional to inhalation. More particularly, by connecting the inlet of the sampling head being used to a rapid response flow meter, and by the operator entering a calibration mode via the PSP menu, both the pump flow and the valve actuation may be calibrated. By the operator selecting pump calibration mode, the valves are automatically set for 100% duty cycle air flow through the PSP collection medium and the operator may adjust the pump flow using the selection buttons on the PSP until the flow meter reading matches the desired flow. Then after setting the flow meter for a long averaging time period, and putting the PSP in valve calibration mode, the PSP will energize the valve(s) for example at 50% duty cycle, and the operator will use the buttons on the PSP to increase or decrease the time the valve(s) is actuated until the flow meter indicates that the averaged flow is 50% of that for which the pump flow was calibrated. Valve calibration may continue for other selected duty cycles such that the PSP computer will store a calibration curve that will assure that valve(s) switching closely follows that commanded. Moreover, since valve response time is independent of the magnitude of change in inhalation, a simple calibration curve results as opposed to prior art PSPs where the magnitude of change in pump speed is dependent upon the magnitude of change in inhalation.

Referring to FIG. 4, a PSP impact sampling head 40 is shown which can be substituted for the sampling head 12 and which is used for size-selective sampling of particulates. The impact sampling head 40 includes all the same components as represented in the sampling head 12 detailed in FIG. 2, with the exception that the two charcoal tubes 16 and 18 of the previously disclosed design are replaced with two impact samplers (a) 42 and 44. The cylindrical plastic enclosure depicted in the sampling head 12 further is shortened such that the two impact samplers extend outside of the plastic enclosure. Other features including the air tube 24 and control cable 28 with extending plug end 34 are again illustrated as previously shown in gas and vapor sampling head 12. An integrated circuit temperature sensor 45 (see also at 32 in FIG. 2) with fast response includes attached wires 47 (see also 30 in FIG. 2) that together with additional wires extending from the valve(s) 14 goes to the cable 28 previously disclosed in FIG. 2 that in turn plugs into the PSP enclosure via plug end 34 which engages a control cable connector 36 (again in FIG. 1) also located atop the PSP in proximity to the air tube connector fitting 26. Clips 82 and 83 are provided extending from the impact samplers 42 and 44.

In one non-limiting example, an SKC, Inc. (Eighty Four, Pa.) part number 225-70 IOM Sampler composed of several internal parts and a 25 mm filter element is used as the impact samplers 42 and 44 in the sampling head 40 with internally fitted subassemblies (see interconnecting flexible rubber tubes 46 and miniature 25 μm mesh screen, both at 48, used to protect the miniature valve(s) shown at 50 from any particle breakthrough from the impact samplers 42 and 44. The optional foam insert (internal to 42 and 44 and not shown) functions as the pre-collector. Thus, the impact sampling head may also be used for physiologic sampling of total particulates instead of for size-selective sampling of particulates by removing the foam insert used for pre-collection.

Referring again to FIGS. 3A, 3B and 5, the PSP cyclone sampling head, generally referenced at 38 in FIG. 3B, is used for size-selective sampling of particulates and includes an air sampling cyclone 52 (see also FIG. 3A) with an air inlet 53 on the cylindrical side of the cyclone and with a funnel shaped top 54. It is also understood that the funnel configuration can be substituted by other designs within the scope of the invention, such as in a simplest form including an outlet hole at a base of any funnel or other configuration associated with the sampling head. A modification to the funnel like top includes a small hole drilled such that a brass tube 56 may be inserted and sealed with epoxy so as to provide a alternate an air path to a flexible extension tubing 58 extending to a dummy cassette 60 (see FIG. 3A) that in turn contains a dummy filter and support pad. A further PSP cassette 62 incorporates a collection filter element and support pad, the cassette 62 fitting onto a top of the cyclone funnel 54 (see as again shown in FIG. 3B) and sealed air tight by a rubber o'ring (see at 63 in FIG. 3A) that fits in a groove around the top and outer edge of the cyclone funnel.

As shown at 64 in assembled fashion in FIG. 3B and as further exploded in FIG. 5, a valve manifold assembly is shown and is composed of numerous small parts and fittings, such as further shown in FIG. 5 to include manifold housings 66 and 68 communicable with the PSP 62 and dummy 60 cassettes via duplicate screen 65, washer 67 and inlet 69 components. Also included are gaskets 70, 72 and 74, as well as aluminum airway insert 75 reducing air space within the manifold for assembling the manifold housings 66 and 68 around a further central component 76 in turn engaged by a washer 67 and a fitting 78 at an upper end and which receives an air tube 80 (see FIG. 3B) extending to a vacuum pump.

The assembly 64 connects to an outlet (back) of both cassettes 60 and 62 and assembly 64 further exhibits an outlet barbed port connection to air tube 80 that in turn connects to a barbed fitting, see as previously depicted at 26 in FIG. 1 on the PSP enclosure. Separately, valve control cable 84 includes inner wires 86 connected to the terminals associated with valves 88 mounted (this including a total of six valves with three visibly mounted on the front and three more hidden mounted on the base of the manifold assembly) within the assembly at first ends, and with an opposite end of the valve control cable 84 connecting, via a plug 34, into a mating connector (see also at 36 in FIG. 1) on the PSP enclosure and thereby providing electronic control signals that energized the valve(s) 88 to cause the air flow to switch between the two cassettes 60 and 62. In one non-limiting example, an SKC, Inc. (Eighty Four, Pa.) Respirable Dust Aluminum Cyclone, part number 225-01-02, is utilized as the pre-collector. Also show is clip 90 extending from a top of the manifold in proximity to air tube 80.

In one non-limiting variant, the cyclone 52 exhibits a median cut-point at 4 um at a flow of 2.5 lpm and is machined so that respirable particles will exit the cyclone in the airflow via its funnel shaped outlet and be dispersed onto a filter. The sampling filter is placed inside a 37 mm cassette, see at 62 in FIG. 3B that fits onto the top of the cyclone.

Other features include the PSP unit 10 incorporating a molded plastic case or other material such as aluminum or the like, but preferably of thereto-resistant nature such construction allowing the internal air cavity to be incorporated into the case itself, reducing cost and size. The thermal characteristics of the unit would thus improve, especially in direct sunlight. The ambient air temperature sensors may also be moved to a location outside of the case such as at 32 in FIG. 2 that is shaded from the sun, such as in order that unit's thermal mass does not cause the mass air flow correction factor to be erroneous when positioned in direct sunlight or when the unit is subjected to varying temperature extremes.

Potential applications of the PSP sampling pump in addition to exposure assessment and physiologic sampling of ambient air include incorporating a type of delivery system for patient's or athletes. In a delivery scenario, an air supply of known oxygen concentration is connected into the pump PSP collection filter port while the ambient air would enter the dummy filter port, the pump exhaust thereby becoming the patient's or athlete's air supply. A much higher pump flow rate would be required than the prototype pump designed and built for exposure assessment, given that the concept would be similar. Oxygen can be metered to athletes in proportion to a level of exertion, thereby allowing the athlete to exercise to a level beyond their typical limits. Alternatively, oxygen through the PSP port could be restricted in some correlated manner to simulate high altitudes for athletes needing to train for such an environment. In the instance of a constant flow rate pump being used, some additional means of bleeding off or recycling volume in excess of that inhaled, would be incorporated into the system. Otherwise, feedback is necessary to control the pump flow so as to follow the volume as demanded by inhalation.

Experimentation therefore of the cyclone sampling head 38 for size-selective sampling of particulates as disclosed herein can include, in one non-limiting variant, a plurality of six valves identical to those used in the gas and vapor implementation, the six valves arranged into two banks of three valves each. Utilizing six valves in parallel has been found to reduce the greater pressure drop that is created at the higher flow when used by the cyclone. Three valves are mounted on the front as shown at 88 and the other three valves are mounted on the back side and are therefore not shown.

The assembly of FIG. 1 also illustrates a sensor interactive shirt, such as commercially known in one non-limiting variant as a VivoMetrics, Inc. LifeShirt® system 92 that plugs into the PSP 10, via a cable 94 in order to provide real time physiologic data that is processed each second by equations stored within the PSP computer program in order to estimate inhalation of the user and to control valve operation in the sampling heads, with the flexibility of the computer program embedded in the PSP, enabling other physiologic signal(s) from other hardware to be inputted into the PSP and used to estimate inhalation and to control valve operation.

Accordingly, the present invention discloses a physiologic sampling pump (PSP) which overcomes shortcomings of prior art designs by calibrating and using valves in conjunction with a constant speed pump in order to obviate pump inertia that inherently limits system response, functionality and accuracy. Performance of the PSP is not degraded by pump inertia nor by sluggishness in response caused by a length of air tube (normally 3 feet long and ¼" internal diameter) that connects the pump motor to the collection medium utilized in prior art PSPs nor by size selective sampling errors from varying pump speeds, since the design holds air flow constant and controls PSP sampling rate by calibrated valves that open and close to redirect air flow almost instantaneously.

Additional modifications to the PSP pump extend its potential applications to size selective sampling of aerosols and in which separation of particulates by size is accomplished by using a cyclone or impact sampler subject to a constant flow however, and similar to breathing, providing intermittent sampling of particles, the data from which is compared to reference data in order to plot an efficiency curve.

The present design also accommodates leveraging the use of present or future technologies, which may directly or indirectly provide minute ventilation of a subject user to the end that any of these technologies may be used to the limit of its own accuracy to sample subject user inhalation exposures to airborne contaminants. Accordingly, use of the PSP design realizes the benefits hoped for by prior PSP pump designs, these including more accurate and meaningful determination of subject exposures than is available with standard personal sampling pumps that do not account for variations in breathing rate.

Having described our invention, other and additional preferred embodiments will become apparent to those skilled in the art to which it pertains, and without deviating from the scope of the appended claims.

The invention claimed is:

1. A physiological sampling pump (PSP) for providing rapid response to breathing, comprising:
   a pump body including an outer thermo-resistant housing;
   at least one interchangeable sampling component for collection of an aerosol for accomplishing size selective sampling and total sampling of particulates, said component including at least one interior located valve in communication with said pump body via a first air tube and a second valve control cable;
   said sampling component further comprising a cyclone sampling head used for size-selective sampling of particulates and including an air sampling cyclone with a funnel shaped top;
   a tubing extending from said cyclone sampling head to a first cassette in turn containing a dummy filter and support pad, a further PSP cassette incorporating a collection filter element and support pad and fitting onto a top of said cyclone funnel; and
   said valve rapidly switching in proportional response to variations in inhalation within said sampling component, in order to provide effective test sampling while maintaining constant pump speed and airflow through a pre-collector cyclone component.

2. The invention as described in claim 1, said valve further comprising a plurality of individual valves incorporated into a valve manifold assembly communicable with said first and PSP cassettes.

3. The invention as described in claim 1, further comprising said cyclone sampling head exhibiting a median cut-point at 4 um at a flow of 2.2 1 pm and which is machined so that respirable particles will exit the cyclone in the airflow via its funnel shaped outlet and be dispersed onto a filter.

4. The invention as described in claim 1, further comprising a sensor interactive shirt that plugs into the pump body via a cable in order to provide real time physiologic data that is processed at any desired time interval by an equation stored within a PSP computer program in order to estimate inhalation of the user and to control valve operation in the sampling heads.

5. A physiological sampling pump (PSP) for providing rapid response to breathing, comprising:
   a pump body including an outer thermo-resistant housing;
   at least one interchangeable sampling component for collection of an aerosol for accomplishing size selective sampling and total sampling of particulates, said component including at least one interior located valve in communication with said pump body via a first air tube and a second valve control cable;
   said sampling component further comprising a cyclone sampling head used for size-selective sampling of particulates and including an air sampling cyclone with a funnel shaped top;
   a tubing extending from said cyclone sampling head to a first cassette in turn containing a dummy filter and support pad, a further PSP cassette incorporating a collection filter element and support pad and fitting onto a top of said cyclone funnel;
   said valve further having a plurality of individual valves incorporated into a valve manifold assembly communicable with said first and PSP cassettes; and
   said valve rapidly switching in proportional response to variations in inhalation within said sampling component, in order to provide effective test sampling while maintaining constant pump speed and airflow through a pre-collector component.

6. A physiological sampling pump (PSP) for providing rapid response to breathing, comprising:
   a pump body including an outer thermo-resistant housing;
   at least one interchangeable sampling component for collection of at least one of gases, vapors and aerosols for accomplishing size selective sampling and total sampling of particulates, said component including at least one interior located valve in communication with said pump body via a first air tube and a second valve control cable;
   a sensor interactive shirt that plugs into the pump body via a cable in order to provide real time physiologic data that is processed at any desired time interval by an equation stored within a PSP computer program in order to estimate inhalation of the user and to control valve operation in the sampling components; and
   said valve rapidly switching in proportional response to variations in inhalation within said sampling component, in order to provide effective test sampling while maintaining constant pump speed and airflow through a pre-collector component.

7. A physiological sampling pump (PSP) for providing rapid response to breathing, comprising:
   a pump body including an outer thermo-resistant housing;
   at least one interchangeable sampling component for size selective sampling of particulates, all necessary parts of said sampling component being located downstream of a pre-collector inlet, sampling being further achieved without dilution of an aerosol being sampled by another gas, such as by mixing the aerosol being sampled with another gas in a mixer;
   said component further including at least one interior located valve in communication with said pump body via a first air tube and a second valve control cable; and
   said valve rapidly switching between fully opened and fully closed positions in proportional response to variations in inhalation within said sampling component, in order to provide effective test sampling while maintaining constant pump speed and airflow through a pre-collector component.

8. The invention as described in claim 7, said sampling component further comprising a charcoal tube sampling head used for collection of gases and vapors accessible through an inlet end where two charcoal tubes extend toward in order to pull in external air to be sampled, a first charcoal tube acting as a collection medium, with a second charcoal tube acting as a dummy collection medium to present an approximately equivalent load to a pump motor to help minimize the magnitude of any air perturbations upon valve(s) switching.

9. The invention as described in claim 8, further comprising two short lengths of flexible rubber tubing connecting to outlets of said charcoal tubes, opposite extending ends of said flexible tubes communicating with miniaturized mesh screens used to protect said at least one valve from any particle breakthrough from said charcoal tubes.

10. The invention as described in claim 9, further comprising an integrated circuit temperature sensor incorporated into said sampling component in communication with said control cable via attached wires which, together with additional wires extending from said at least one valve, communicates with said control.

11. The invention as described in claim 7, said sampling component further comprising an impact sampling head for size-selective and total collection of particulates accessible through an inlet end including two impact samplers.

12. The invention as described in claim 11, further comprising two short lengths of flexible rubber tubing connecting to outlets of said impact samplers, opposite extending ends of said flexible tubes communicating with miniaturized mesh screens used to protect said at least one valve from any particle breakthrough from said impact sampler.

13. The invention as described in claim 11, further comprising an integrated circuit temperature sensor incorporated into said sampling component in communication with said control cable via attached wires which, together with additional wires extending from said at least one valve, communicates with said valve.

* * * * *

UNITED STATES PATENT AND TRADEMARK OFFICE
CERTIFICATE OF CORRECTION

| | |
|---|---|
| PATENT NO. | : 8,459,098 B2 |
| APPLICATION NO. | : 12/690550 |
| DATED | : June 11, 2013 |
| INVENTOR(S) | : Larry Alan Lee et al. |

It is certified that error appears in the above-identified patent and that said Letters Patent is hereby corrected as shown below:

In the Claims

At column 9, claim number 3, line number 58, Delete "1 pm", Insert --1pm--.

Signed and Sealed this
Seventeenth Day of June, 2014

Michelle K. Lee
*Deputy Director of the United States Patent and Trademark Office*